(12) United States Patent
Candau

(10) Patent No.: US 6,248,311 B1
(45) Date of Patent: *Jun. 19, 2001

(54) PHOTOPROTECTIVE/COSMETIC COMPOSITIONS COMPRISING BISRESORCINYLTRIAZINE AND BENZOAZOLYL/BENZODIAZOLYL

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,944

(22) Filed: Feb. 14, 2000

(30) Foreign Application Priority Data

Feb. 12, 1999 (FR) .................................................. 99 01732

(51) Int. Cl.⁷ .............................. A61K 7/42; A61K 7/44; A61K 7/00
(52) U.S. Cl. .............................. 424/59; 424/60; 424/400; 424/401; 514/241
(58) Field of Search ............................... 424/59, 60, 400, 424/401; 514/241

(56) References Cited

FOREIGN PATENT DOCUMENTS

| 0 350 763 | 6/1997 | (CH) . |
| 195 48 014 | 6/1997 | (DE) . |
| 0 669 323 | 8/1995 | (EP) . |
| 0 775 698 | 5/1997 | (EP) . |
| 0 824 909 | 2/1998 | (EP) . |
| 0 878 469 | 11/1998 | (EP) . |

*Primary Examiner*—Shelley A. Dodson
(74) *Attorney, Agent, or Firm*—Burns, Doane, Swecker & Mathis, L.L.P.

(57) ABSTRACT

Topically applicable sunscreen/cosmetic compositions well suited for the synergistically enhanced photoprotection of human skin and/or hair against the damaging effects of UV-irradiation, particularly solar radiation, comprise synergistically UV-photoprotecting effective amounts of each of (a) at least one bisresorcinyltriazine compound, and (b) at least one compound containing two benzoazolyl groups, or at least one benzodiazolyl group, formulated into a topically applicable, cosmetically acceptable vehicle, diluent or carrier therefor.

32 Claims, No Drawings

PHOTOPROTECTIVE/COSMETIC COMPOSITIONS COMPRISING BISRESORCINYLTRIAZINE AND BENZOAZOLYL/BENZODIAZOLYL

CROSS-REFERENCE TO PRIORITY APPLICATION

This application claims priority under 35 U.S.C. §119 of FR-99/01732, filed Feb. 12, 1999, hereby expressly incorporated by reference.

BACKGROUND OF THE INVENTION

1. Technical Field of Invention

The present invention relates to novel cosmetic compositions for topical application, for the photoprotection of the skin and/or hair against ultraviolet radiation (such compositions hereinafter simply designated "antisun," "sunscreen" or "photoprotective" compositions) and to the use of the same for the cosmetic applications indicated above.

This invention more especially relates to the aforesaid sunscreen/cosmetic compositions comprising, formulated into a cosmetically acceptable vehicle, diluent or carrier therefor, binary combination of (a) at least one bisresorcinyltriazine compound, as a first screening agent, and (b) at least one compound containing at least two benzoazolyl groups and/or at least one compound containing at least one benzodiazolyl group, as a second screening agent, the said first and second screening agents being present in the subject compositions in proportions eliciting a synergistic effect with regard to the protection factors conferred.

2. Description of the Prior Art

It is known to this art that light radiation of wavelengths of from 280 nm to 400 nm promotes tanning of the human epidermis and that irradiation with wavelengths of from 280 to 320 nm, i.e., UV-B radiation, cause erythemas and skin burns which may be harmful to the development of natural tanning; this UV-B radiation must therefore be screened from the skin.

It is also known to this art that UV-A radiation, with wavelengths of from 320 to 400 nm, which causes tanning of the skin, can also adversely affect it, in particular in the case of sensitive skin or of skin continually exposed to solar radiation. UV-A rays cause, in particular, a loss in the elasticity of the skin and the appearance of wrinkles, resulting in premature aging. Such irradiation promotes the triggering of the erythemal reaction or accentuates this reaction in certain individuals and can even be the cause of phototoxic or photoallergic reactions. It is therefore desirable to also screen out UV-A radiation.

A wide variety of cosmetic compositions for the photoprotection (UV-A and/or UV-B) of the skin are known to this art.

These photoprotective/sunscreen compositions are typically emulsions of oil-in-water type (namely, a cosmetically acceptable vehicle, diluent or carrier comprising a continuous aqueous dispersing phase and a non-continuous oily dispersed phase) which contains, in various concentrations, one or more conventional lipophilic and/or hydrophilic organic screening agents capable of selectively absorbing harmful UV radiation. These screening agents (and their amounts) are selected according to the desired protection factor (the protection factor (PF) being expressed mathematically by the ratio of the irradiation time required to attain the erythemogenic threshold with the UV screening agent to the time required to attain the erythemogenic threshold without UV screening agent).

SUMMARY OF THE INVENTION

It has now surprisingly and unexpectedly been determined that the binary combination of two specific sunscreen compounds already per se known to this art provided synergistically active sunscreen/antisun compositions exhibiting markedly improved protection factors.

Briefly, the present invention features novel cosmetic compositions, in particular photoprotective/sunscreen compositions, comprising, in a cosmetically acceptable vehicle, diluent or carrier, (a) at least one bisresorcinyltriazine compound, as a first screening agent, and (b) at least one compound containing at least two benzoazolyl groups and/or at least one compound containing at least one benzodiazolyl group, as a second screening agent, the said first and second screening agents being present in the subject compositions in proportions eliciting a synergistic effect with regard to the protection factors conferred.

The present invention also features the use of the subject compositions in the production of cosmetic compositions suited for the protection of the skin and/or hair against the deleterious effects of ultraviolet radiation, in particular solar radiation.

This invention thus also features cosmetic regime/regimen for the photoprotection of skin and/or hair against the damaging effects of ultraviolet radiation, in particular solar radiation, which essentially entails topically applying onto the skin/hair an effective photoprotecting amount of a composition in accordance herewith.

DETAILED DESCRIPTION OF BEST MODE AND SPECIFIC/PREFERRED EMBODIMENTS OF THE INVENTION

More particularly according to the present invention, novel cosmetic or dermatological compositions, in particular antisun/sunscreen compositions, are provided which comprise, formulated into a cosmetically acceptable vehicle, diluent or carrier therefor:

(a) at least one bisresorcinyltriazine compound, as a first screening agent, and (b) at least one compound containing at least two benzazolyl groups and/or at least one compound containing at least one benzodiazolyl group, as a second screening agent, the said first and second screening agents being present in the subject compositions in proportions eliciting a synergistic effect with regard to the protection factors conferred.

By the term "containing at least two enzoazolyl groups" is intended, per molecule, at least two groups of the benzoxazolyl, benzothiazolyl or benzimidazolyl type.

By the term "containing at least one benzodiazolyl group" is intended, per molecule, a group of the benzodioxazolyl, benzodithiazolyl or benzodiimidazolyl type.

The bisresorcinyltriazine compounds according to the invention are preferably selected from among those having the following structural formula:

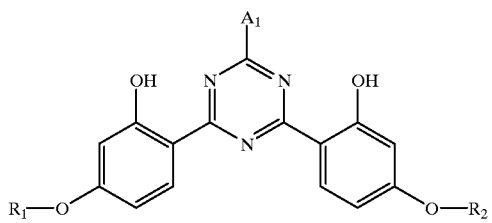
(I)

in which (i) the $R_1$ and $R_2$ radicals, which may be identical or different, are each a $C_3$–$C_{18}$ alkyl radical, a $C_2$–$C_{18}$ alkenyl radical, or a residue of the formula —$CH_2$—CH(OH)—$CH_2$—$OT_1$ wherein $T_1$ is a hydrogen atom, or a $C_1$–$C_8$ alkyl radical; or (ii) the $R_1$ and $R_2$ radicals, which again may be identical or different, are each a residue of the following formula (1):

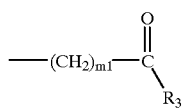
(1)

in which $m_1$ is a number ranging from 1 to 3; and $R_3$ is a hydroxyl group, a $C_1$–$C_5$ alkyl radical which is unsubstituted or substituted by one or more hydroxyl groups, a $C_1$–$C_5$ alkoxy radical, an amino group; a mono -or di($C_1$–$C_5$)alkylamino radical, a metal cation M, or a residue having one of the following formulae (2) to (7):

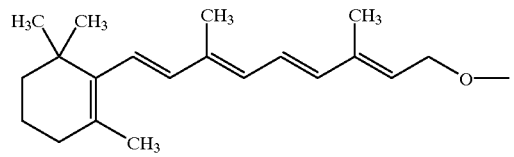
(2)

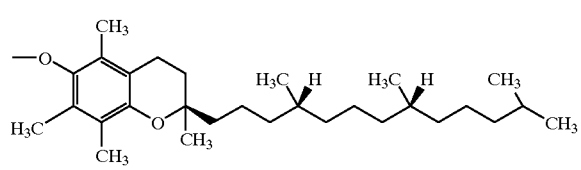
(3)

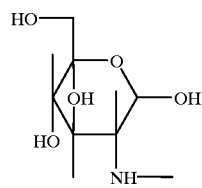
(4)

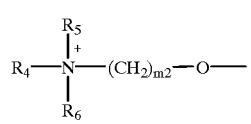
(5)

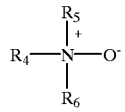
(6)

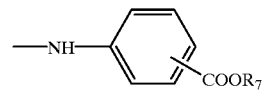
(7)

in which the $R_4$, $R_5$ and $R_6$ radicals, which may be identical or different, are each a $C_1$–$C_{14}$ alkyl radical which is unsubstituted or substituted by one or more hydroxyl groups; $R_7$ is a hydrogen atom, a metal cation M, a $C_1$–$C_5$ alkyl radical, or a residue of formula —$(CH_2)_{m2}$—$OT_1$ where $m_2$ is a number ranging from 1 to 4 and $T_1$ is as defined above; or (iii) the $R_1$ and $R_2$ radicals, which again may be identical or different, are each a residue of the following formula (8):

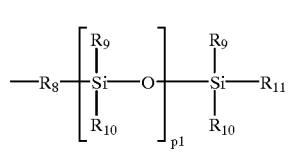
(8)

in which $R_8$ is a covalent bond, a linear or branched $C_1$–$C_4$ alkyl radical, or a residue of formula —$C_{m4}H_{2m4}$— or —$C_{m4}H_{2m4}$—O— wherein $m_4$ is a number ranging from 1 to 4; $p_1$ is a number ranging from 0 to 5; the $R_9$, $R_{10}$ and $R_{11}$ radicals, which may be identical or different, are each a $C_1$–$C_{18}$ alkyl radical, a $C_1$–$C_{18}$ alkoxy radical or a residue of the formula:

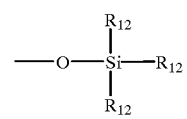
(9)

wherein $R_{12}$ is a $C_1$–$C_5$ alkyl radical; $A_1$ is a residue having one of the following formulae:

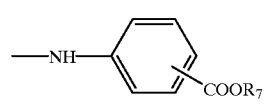
(7)

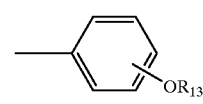
(10)

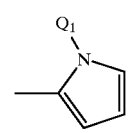
(11)

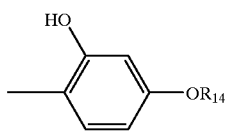

in which $R_7$ is as defined above; $R_{13}$ is a hydrogen atom, a $C_1-C_{10}$ alkyl radical, a radical of formula $-(CH_2CHR_{16}-O)_{n1}R_7$ wherein $n_1$ is a number ranging from 1 to 16 and $R_{16}$ is a hydrogen atom or a methyl radical, or a residue of the formula $-CH_2-CH(OH)-CH_2OT_1$ wherein $T_1$ is as defined above; $Q_1$ is a $C_1-C_{18}$ alkyl radical; and $R_{14}$ is a radical having the formula (1):

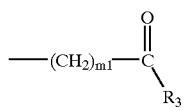

as described above.

In the above formulae (I) and (1) to (12);

- the alkyl radicals are linear or branched and advantageously are selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl and octadecyl;
- the $C_2-C_{18}$ alkenyl radicals are advantageously selected, for example, from among allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isodedecenyl and n-octadec-4-enyl;
- the alkoxy radicals are linear or branched and are advantageously selected, for example, from among methoxy, ethoxy, n-propoxy, isopropoxy, n-butoxy, sec-butoxy, tert-butoxy, amyloxy, isoamyloxy and tert-amyloxy;
- the mono- or dialkylamino radicals are advantageously selected, for example, from among methylamino, ethylamino, propylamino, n-butylamino, sec-butylamino, tert-butylamino, pentylamino, dimethylamino, diethylamino, dibutylamino and methylethylamino;
- the metal cations M are alkali metal, alkaline earth metal, or metal cations advantageously selected, for example, from among lithium, potassium, sodium, calcium, magnesium, copper and zinc.

The bisresorcinyltriazine compounds of formula (I) of the invention are screening agents already per se known to this art. They are described and prepared according to the syntheses illustrated in described in EP-A-0,775,698 and EP-A-0,878,469 hereby expressly incorporated by reference.

Exemplary bisresorcinyltriazine compounds of formula (I) are those in which the $A_1$ radical denotes para-methoxyphenyl or 4-ethoxyphenyl and the $R_1$ and $R_2$ radicals, which may be identical or different, are each a radical having the structure:

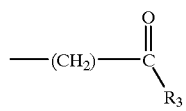

in which $R_3$ is selected from among:
- tert-butyloxy;
- OH;
- OM, wherein M is an alkali metal or alkaline earth metal cation or a cation selected from among copper, magnesium or zinc;
- a group having the structure:

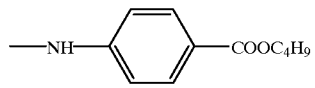

- a group having the structure $O^-N^+(CH_2CH_2OH)_3$;
- a group having the structure:

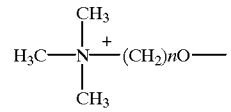

wherein n ranges from 2 to 16;
- a group having the structure:

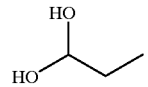

or a group having the structure:

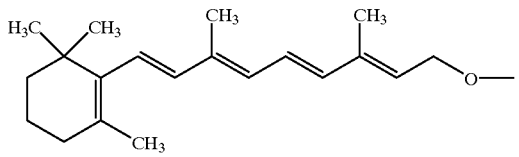

Also exemplary is a bisresorcinyltriazine compound having the formula (I) in which the $A_1$ radical denotes para-hydroxyphenyl and the $R_1$ and $R_2$ radicals simultaneously are each a group having the structure:

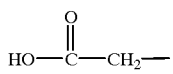

Particularly representative compounds of formula (I) are:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}6-(4-methoxyphenyl)-1,3,5-triazine;
2,4-bis{[4-(2-ethylhexyloxy)-2-hydroxy]phenyl}-6-[4-(2-methoxyethyloxycarbonyl)phenylamino]-1,3,5-triazine;
2,4-bis{[4-(tris(trimethylsiloxy)silylpropyloxy)-2-hydroxy]phenyl}-6-(4-methoxyphenyl)-1,3,5-triazine;

2,4-bis{[4-(2''-methylpropenyloxy)-2-hydroxy]phenyl}-6-(4-methoxyphenyl)-1,3,5-triazine;

2,4-bis{[4-(1', 1', 1', 3', 5', 5', 50'-heptamethyltri-siloxy-2''-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-(ethoxycarbonyl)phenylamino]-1,3,5-triazine;

2,4-bis{[4-(2-ethylhexyloxy)-2-hydroxy]phenyl}-6-(1-methylpyrrol-2-yl)-1,3,5-triazine.

The bisresorcinyltriazine compounds which are more particularly preferred according to the invention are selected from the group consisting of:

2,4-bis{[4-(2-ethylhexyloxy)-2-hydroxy]phenyl}-6-(4-methoxyphenyl)-1,3,5-triazine;

2,4-bis{[4-(tris(trimethylsiloxy)silylpropyloxy)-2-hydroxy]phenyl}-6-(4-methoxyphenyl)-1,3,5-triazine;

2,4-bis{[4-(1', 1', 1', 3', 5', 5', 5'-heptamethyltrisiloxy-2''-methylpropyloxy)-2-hydroxy]phenyl}-6-(4-methoxyphenyl)-1,3,5-triazine.

The sunscreen or sunscreens of the bisresorcinyltriazine compound type are advantageously formulated into the compositions according to the invention at a concentration ranging from 0.1% to 15%, preferably from 0.2% to 10%, by weight with respect to the total weight of the composition.

Preferred compounds containing at least two benzoazolyl groups in accordance with the invention are those having the following structural formula (II):

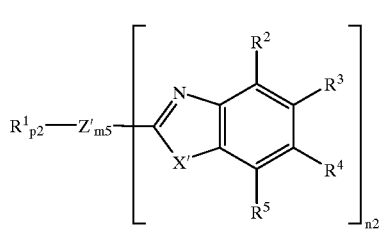

(II)

in which Z' is an organic residue with a valency of $(p_2+n_2)$ comprising one or more double bonds which are positioned such that the double bond completes the system of double bonds of at least two benzoazolyl groups as defined inside the brackets, in order to form a completely conjugated structural unit; X' is S, O or $NR^6$; $R^1$ is a hydrogen atom, a $C_1$–$C_{18}$ alkyl radical, a $C_1$–$C_4$ alkoxy radical, a $C_5$–$C_{15}$ aryl radical, a $C_2$–$C_{18}$ acyloxy radical, $SO_3Y'$ or $COOY'$; the $R^2$, $R^3$, $R^4$ and $R^5$ radicals, which may be identical or different, are each a nitro group, or a radical $R^1$; $R^6$ is a hydrogen atom, a $C_1$–$C_4$ alkyl radical or a $C_1$–$C_4$ hydroxyalkyl radical; Y' is a hydrogen atom, Li, Na, K, $NH_4$, ½Ca, ½Mg, ⅓Al, or a cation resulting from the neutralization of a free acid group by a nitrogenous organic base; $m_5$ is 0 or 1; $n_2$ is a number ranging from 2 to 6; $p_2$ is a number ranging from 1 to 4; with the proviso that $p_2+n_2$ does not exceed the value 6.

The compounds of formula (II) according to the invention are water-soluble UV-A screening agents described in EP-A-0,669,323. They are described and prepared according to the syntheses illustrated in U.S. Pat. No. 2,463,264 and EP-A-0,669,323 hereby expressly incorporated by reference.

Preferred compounds of formula (II) are those in which the Z' group is selected from among:

(a) an unsaturated linear aliphatic $C_2$–$C_6$ hydrocarbonaceous radical which can be interrupted by a $C_5$–$C_{12}$ aryl radical or a $C_4$–$C_{10}$ heteroaryl radical, such as, for example: —CH=CH—, —CH=CH—CH=CH— or

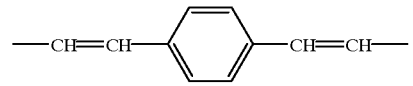

(b) a $C_5$–$C_{15}$ aryl radical which can be interrupted by an unsaturated linear aliphatic $C_2$–$C_6$ hydrocarbonaceous radical, such as, for example, the following:

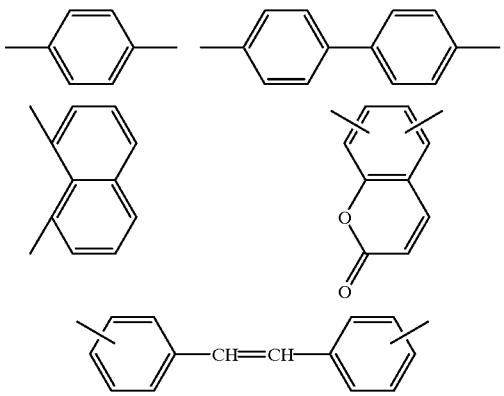

(c) a $C_3$–$C_{10}$ heteroaryl radical, such as, for example, the following:

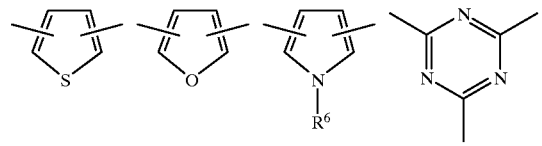

wherein $R^6$ is as defined above, with the proviso that said Z' radicals as defined in paragraphs (a), (b) and (c) may be substituted by $C_1$–$C_6$ alkyl, $C_1$–$C_6$ alkoxy, phenoxy, hydroxyl, methylenedioxy or amino radicals, the amino radicals optionally being substituted by one or two $C_1$–$C_5$ alkyl radicals.

Exemplary compounds of formula (II) are those having the following formulae and salts thereof:

Compound 1

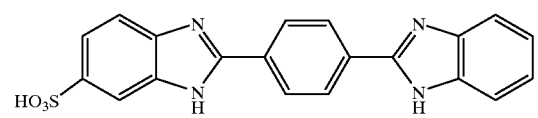

Compound 2

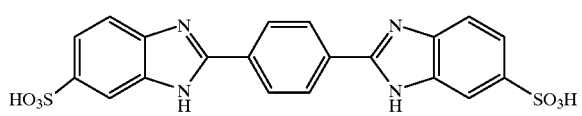

-continued

Compound 3

Compound 4

Compound 5

Compound 6

Compound 7

Compound 8

Compound 9

Compound 10

Compound 11

Compound 12

Compound 13

Compound 14

Compound 15

Compound 16
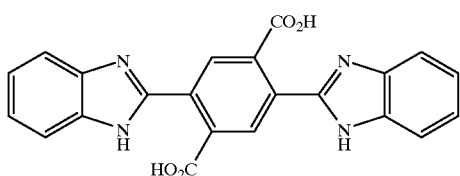

Compound 17
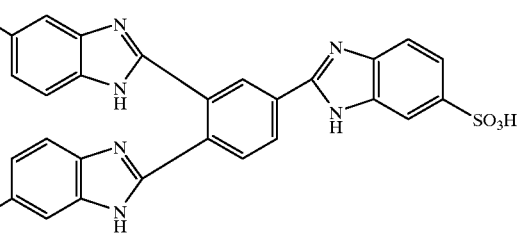

Compound 18
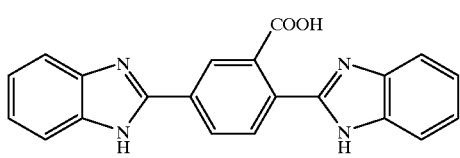

Compound 19
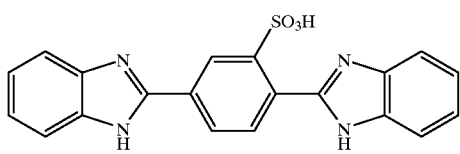

Compound 20
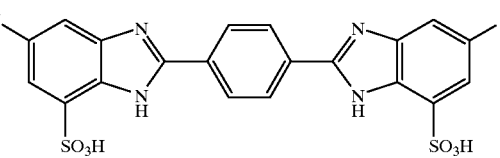

Compound 21
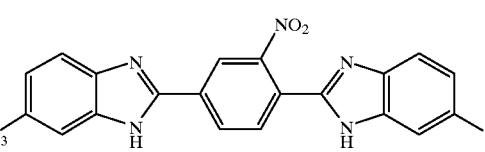

Compound 22
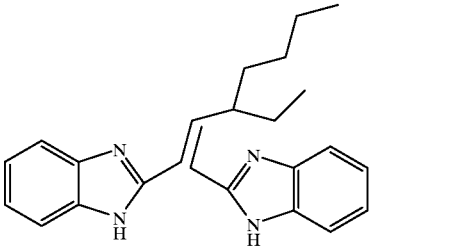

Compound 23
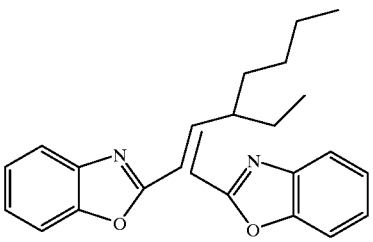

Compound 24
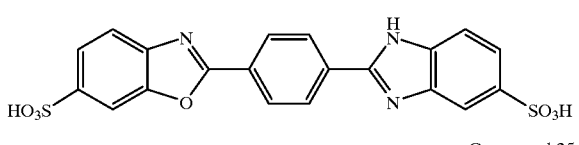

Compound 25
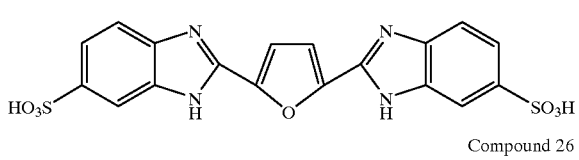

Compound 26
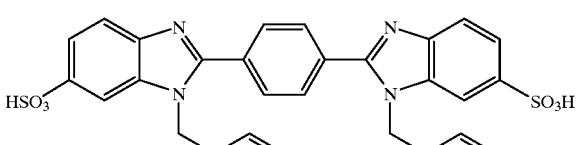

Compound 27
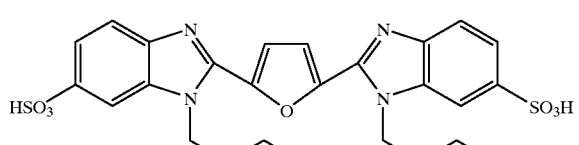

Among such compounds, particularly preferred are 1,4-bis(benzimidazolyl)-phenylene-3,3', 5,5'-tetrasulponic acid (Compound 4) and its salts having the following structure:

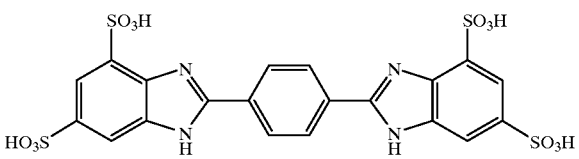

Also exemplary such compounds containing at least two benzoazolyl groups are the following compounds and salts thereof:

Compound 28

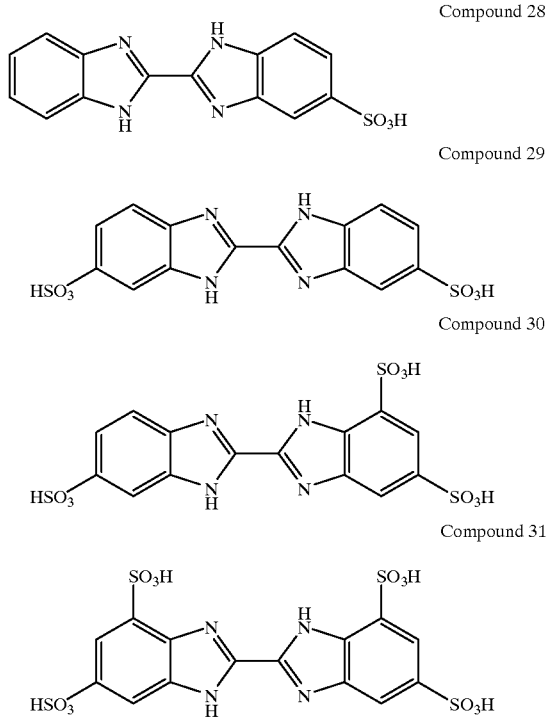

Compound 29

Compound 30

Compound 31

Exemplary compounds containing at least one benzodiazolyl group according to the invention are the following compounds and salts thereof:

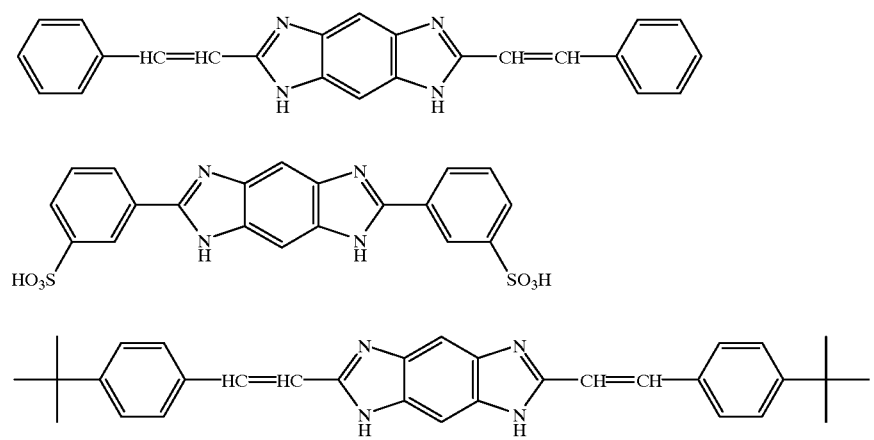

Compound 32

Compound 33

Compound 34

The compound or compounds containing benzoazolyl or benzodiazolyl groups in accordance with the invention are advantageously formulated into the subject compositions at a concentration ranging from 0.1% to 15%, preferably from 0.2% to 10%, by weight with respect to the total weight of the composition.

As indicated above, in a characteristic embodiment of the present invention, the subject two types of sunscreens are each present in the final composition in respective proportions such that a substantial and significant synergistic effect is obtained with regard to the protection factor conferred by the resulting combination.

In addition and generally, it should be noted that the concentrations and ratios of the bisresorcinyltriazine compounds and the compounds containing benzoazolyl or benzodiazolyl groups as described above are selected such that the sun protection factor of the final composition is preferably at least 2.

In another preferred embodiment of the present invention, the cosmetically acceptable medium (vehicle, diluent or carrier) in which the various screening agents are present is an emulsion of oil-in-water type.

The sunscreen/antisun cosmetic compositions according to the invention can, of course, contain one or more additional hydrophilic or lipophilic sunscreens which are active in the UV-A and/or UV-B regions (absorbers), other than the two screening agents indicated above. These additional screening agents are advantageously selected, in particular, from among cinnamic derivatives, salicylic derivatives, camphor derivatives, triazine derivatives other than those described above, such as those described in EP-863,145, EP-517,104, EP-570,838 and EP-796,851, benzophenone derivatives, dibenzoylmethane derivatives, β, β-diphenylacrylate derivatives, benzimidazole derivatives other than those described above, p-aminobenzoic acid derivatives, or screening polymers and screening silicones, such as those described in WO-93/04665.

Exemplary such additional sunscreens which are active in the UV-A and/or UV-B ranges include:

p-aminobenzoic acid;
oxyethylenated (25 mol) p-aminobenzoate;
2-ethylhexyl p-dimethylaminobenzoate;
N-oxypropylenated ethyl p-aminobenzoate;
glycerol p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;

2-ethylhexyl 2-cyano-3,3-diphenylacrylate;
ethyl 2-cyano-3,3-diphenylacrylate;
2-phenylbenzimidazole-5-sulfonic acid and its salts;
3-(4'-trimethylammonio)benzylidenebornan-2-one methyl sulfate;
2-hydroxy-4-methoxybenzophenone;
2-hydroxy-4-methoxybenzophenone-5-sulphonate;
2,4-dihydroxybenzophenone;
2,2', 4,4'-tetrahydroxybenzophenone;
2,2'-dihydroxy-4,4'-dimethoxybenzophenone;
2-hydroxy-4-(n-octoxy)benzophenone;
2-hydroxy-4-methoxy-4'-methylbenzophenone;
urocanic acid;
benzene-1,4-di(3-methylidene-10-camphorsulfonic acid) and its salts;
α-(2-oxoborn-3-ylidene)toluene-4-sulfonic acid and its salts;
3-(4'-sulfobenzylidene)bornan-2-one and its salts;
3-(4'-methylbenzylidene)-d,l-camphor;
3-benzylidene-d,l-camphor;
2,4,6-tris[p-(2'-ethylhexyl-1'-oxycarbonyl)anilino]-1,3,5-triazine;
2-[p-(tert-butylamido)anilino]-4,6-bis[(p-(2'-ethyl-hexyl-1'-oxycarbonyl)anilino]-1,3,5-triazine;
the polymer of N-[(2- and 4-)[(2-oxoborn-3-ylidene)-methyl]benzyl]acrylamide;
drometrizole trisiloxane (INC designation);
polyorganosiloxanes comprising a malonate functional group.

The compositions according to the invention can also contain agents for the artificial tanning and/or browning of the skin (self-tanning agents), such as, for example, dihydroxyacetone (DHA)

The cosmetic compositions according to the invention can also contain pigments or alternatively nanopigments (mean size of the primary particles: generally ranging from 5 nm to 100 nm, preferably from 10 nm to 50 nm) comprising metal oxides which are coated or uncoated, such as, for example, titanium dioxide (amorphous or crystallized in the rutile and/or anatase form), iron oxide, zinc oxide, zirconium oxide or cerium oxide nanopigments which are all UV photoprotective agents per se well known. Furthermore, alumina and/or aluminum stearate are conventional coating agents. Such coated or uncoated metal oxide nanopigments are described, in particular in EP-A-0,518,772 and EP-A-0,518,773.

The compositions of the invention can additionally contain conventional cosmetic additives and adjuvants selected, in particular, from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, propellants, basifying or acidifying agents, dyes, colorants, or any other ingredient commonly formulated into cosmetics, in particular, for the production of antisun/sunscreen compositions formulated as emulsions.

Exemplary fatty substances include oils or waxes or their mixtures and they also comprise fatty acids, fatty alcohols and fatty acid esters. The oils are selected from among animal, vegetable, mineral or synthetic oils and in particular from liquid petrolatum, liquid paraffin, volatile or non-volatile silicone oils, isoparaffins, poly-α-olefins, or fluorinated and perfluorinated oils. Likewise, the waxes are advantageously selected from among animal, fossil, vegetable, mineral or synthetic waxes per se known to this art.

Exemplary organic solvents include the lower alcohols and polyols.

The thickeners as advantageously selected, in particular, from among crosslinked homopolymers of acrylic acid, or modified or unmodified guar gums and celluloses, such as hydroxypropylated guar gum, methylhydroxyethyl-cellulose, hydroxypropylmethyl cellulose or hydroxyethyl-cellulose.

One skilled in this art will of course take care to select this or these optional additional compounds and/or the amounts thereof such that the advantageous properties, in particular the sun protection factors, intrinsically provided by the binary combination in accordance with the invention are not, or are not substantially, adversely affected by the envisaged addition or additions.

The compositions of the invention are easioly formulated according to techniques well known to this art, in particular those suited for the formulations of emulsions of oil-in-water or water-in-oil type.

Such compositions can be provided, in particular, in the form of a simple or complex emulsion (OW, W/O, O/W/O or W/O/W), such as a cream, a milk, a gel or a cream gel, a lotion, an ointment, a powder or a solid tube or stick and can optionally be packaged as an aerosol and provided in the form of a foam or spray.

When formulated as an emsulsion, the aqueous phase thereof can comprise a non-ionic vesicular dispersion prepared according to known techniques (Bangham, Standish and Watkins, *J. Mol. Biol.*, 13, 238 (1965), FR 2,315,991 and FR 2,416,008).

The cosmetic compositions of the invention are useful for protecting the human epidermis or the hair against ultraviolet rays, as an antisun/sunscreen composition or as a makeup product.

When the cosmetic compositions according to the invention are used for the photoprotection of the human epidermis against UV irradiation or as sunscreen compositions, they can be provided in the form of a suspension or dispersion in solvents or fatty substances, in the form of a non-ionic vesicular dispersion, or in the form of an emulsion, preferably of oil-in-water type, such as a cream or a milk, in the form of an ointment, gel, cream gel, solid tube, stick, aerosol foam or spray.

When the cosmetic compositions according to the invention are used for the protection of the hair, can be provided in the form of a shampoo, lotion, gel, emulsion or non-ionic vesicular dispersion and can constitute, for example, a rinse-out composition, to be applied before or after shampooing, before or after dyeing or bleaching and before, during or after permanent-waving or hair straightening, a styling or treating lotion or a styling or treating gel, a lotion or a gel for blow drying or hair setting, or a composition for permanent-waving or straightening, dyeing or bleaching the hair.

When the subject compositions are used as a product for making up the eyelashes, eyebrows or skin, such as a treatment cream for the epidermis, foundation, lipstick, eyeshadow, face powder, mascara or eyeliner, they can be provided in the anhydrous or aqueous, pasty or solid form, such as oil-in-water or water-in-oil emulsions, non-ionic vesicular dispersions, or suspensions.

For example, for the antisun/sunscreen formulations in accordance with the invention which comprise a vehicle of oil-in-water emulsion type, the aqueous phase (comprising in particular the hydrophilic screening agents) generally constituted from 50% to 95% by weight, preferably from 70% to 90% by weight, with respect to the total weight of the formulation, the oily phase (comprising in particular the lipophilic screening agents) from 5% to 50% by weight, preferably from 10% to 30% by weight, with respect to the total weight of the formulation, and the (co)emulsifier(s) from 0.5% to 20% by weight, preferably from 2% to 10% by weight, with respect to the total weight of the formulation.

As hereinbefore indicated, the present invention also features a regime/regimen for the cosmetic treatment of the skin or hair, to protect these against the deleterious effects of UV radiation, comprising topically applying, to the skin or hair, an effective photoprotecting amount of a subject cosmetic composition.

In order to further illustrate the present invention and the advantages thereof, the following specific examples are given, it being understood that same are intended only as illustrative and in nowise limitative.

In said examples, all parts and percentages are given by weight.

The following three (3) compositions according to the invention were formulated via conventional cosmetic technique.

EXAMPLE 1

| COMPOSITION | Example 1 |
|---|---|
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{ [4-(2-ethylhexyloxy)-2-hydroxy]-phenyl}-6-(4-methoxyphenyl)-1,3,5-triazine | 2 g |
| Glycerol | 15 g |
| 1,4-Bis(benzimidazolyl)phenylene-3,3',5,5'-tetrasulfonic acid | 2 g |
| Triethanolamine | q.s. pH 7 |
| Preservatives | q.s. |
| Demineralized water, q.s. for | 100 g |

EXAMPLE 2

| COMPOSITION | Example 2 |
|---|---|
| Glycerol mono/distearate/polyethylene glycol (100 EO) stearate mixture (Arlacel 165 FL, ICI) | 2 g |
| Stearyl alcohol (Lanette 18, Henkel) | 1 g |
| Palm oil stearic acid (Stéarine TP, Stéarinerie Dubois) | 2.5 g |
| Polydimethylsiloxane (Dow Corning 200 Fluid, Dow Corning) | 0.5 g |
| Benzoate of $C_{12}/C_{15}$ alcohols (Witconol TN, Witco) | 20 g |
| Triethanolamine | 0.5 g |
| 2,4-Bis{ [4-(tris(trimethylsiloxy)silyl-propyloxy)-2-hydroxy]phenyl}-6-(4-methoxy-phenyl)-1,3,5-triazine | 2.5 g |
| Glycerol | 5 g |
| Hexadecyl phosphate, potassium salt (Amphisol K, Hoffman-Laroche) | 1 g |
| Polyacrylic acid (Synthalen K, 3V) | 0.3 g |
| Hydroxypropyl methyl cellulose (Methocel F4M, Dow Chemical) | 0.1 g |
| 1,4-Bis(benzimidazolyl)phenylene-3,3',5,5'-tetrasulfonic acid | 1.5 g |
| Triethanolamine | q.s. pH 7 |
| Preservatives | q.s. |
| Demineralized water, q.s. for | 100 g |

EXAMPLE 3

| COMPOSITION | Example 3 |
|---|---|
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{ [4-(1',1',1',3',5',5',5'-hepta-methyltrisiloxy-2"-methylpropyloxy)-2-hydroxy]phenyl}-6-(4-methoxyphenyl)-1,3,5-triazine | 2 g |
| Glycerol | 15 g |
| 1,4-Bis(benzimidazolyl)phenylene-3,3',5,5'-tetrasulfonic acid | 1.5 g |
| Triethanolamine | q.s. pH 7 |
| Preservatives | q.s. |
| Demineralized water, q.s. for | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising synergistically UV-photoprotecting effective amounts of each of (a) at least one bisresorcinyltriazine compound, and (b) at least one compound containing at least two benzoazolyl groups per molecule and/or at least one compound containing, per molecule, at least one benzodiazolyl group, formulated into a topically applicable, cosmetically acceptable vehicle, diluent or carrier therefor.

2. The sunscreen/cosmetic composition as defined by claim 1, said at least one bisresorcinyltriazine compound having the structural formula:

(I)

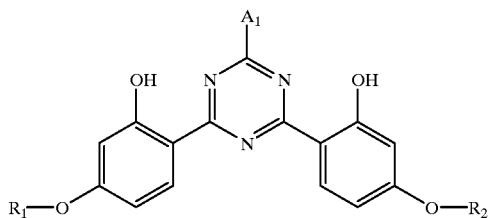

in which (i) the $R_1$ and $R_2$ radicals, which may be identical or different, are each a $C_3$–$C_{18}$ alkyl radical, a $C_2$–$C_{18}$ alkenyl radical, or a residue of formula —$CH_2$—$CH(OH)$—$CH_2$—$OT_1$ wherein $T_1$ is a hydrogen atom, or a $C_1$–$C_8$ alkyl radical; or (ii) the $R_1$ and $R_2$ radicals, which again may be identical or different, are also each a residue of the following formula (1):

(1)

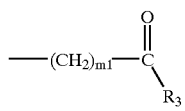

in which $m_1$ is a number ranging from 1 to 3; $R_3$ is a hydroxyl group, a $C_1$–$C_5$ alkyl radical which is unsubstituted or substituted by one or more hydroxyl groups, a $C_1$–$C_5$ alkoxy radical, an amino group; a mono- or di($C_1$–$C_5$)alkylamino radical, a metal cation M, or a residue having one of the following formulae (2) to (7):

(2)

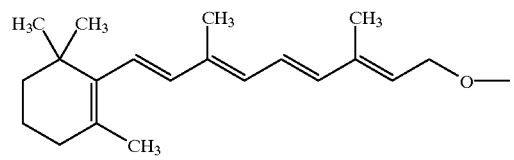

(3)

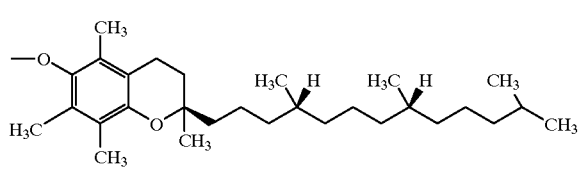

(4)

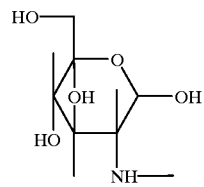

(5)

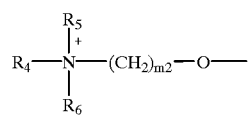

(6)

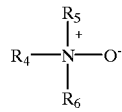

(7)

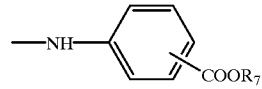

in which the $R_4$, $R_5$ and $R_6$ radicals, which may be identical or different, are each a $C_1$–$C_4$ alkyl radical which is unsubstituted or substituted by one or more hydroxyl groups; $R_7$ is a hydrogen atom, a metal cation M, a $C_1$–$C_5$ alkyl radical or a residue of formula —$(CH_2)_{m2}$—$OT_1$ wherein $m_2$ is a number ranging from 1 to 4 and $T_1$ is as defined above; or (iii) the $R_1$ and $R_2$ radicals, which again may be identical or different, are also each a residue of the following formula (8):

(8)

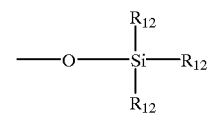

in which $R_8$ is a covalent bond, a linear or branched $C_1$–$C_4$ alkyl radical, or a residue of formula —$C_{m4}H_{2m4}$— or —$C_{m4}H_{2m4}$—O— wherein $m_4$ is a number ranging from 1 to 4; $p_1$ is a number ranging from 0 to 5; the $R_9$, $R_{10}$ and $R_{11}$ radicals, which may be identical or different, are each a $C_1$–$C_{18}$ alkyl radical, a $C_1$–$C_8$ alkoxy radical, or a residue of the formula:

(9)

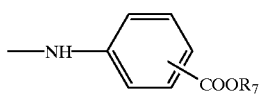

wherein $R_{12}$ is a $C_1$–$C_5$ alkyl radical; $A_1$ is a residue having one of the following formulae:

(7)

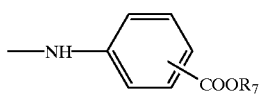

(10)

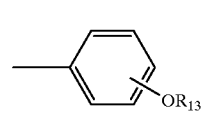

(11)

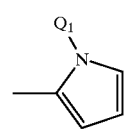

-continued (12)

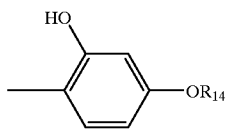

in which $R_7$ is as defined above; $R_{13}$ is a hydrogen atom, a $C_1$–$C_{10}$ alkyl radical, a radical of formula —$(CH_2CHR_{16}$—$O)_{n1}R_7$ wherein $n_1$ is a number ranging from 1 to 16 and $R_{16}$ is a hydrogen atom or methyl, or a residue of formula —$CH_2$—$CH(OH)$—$CH_2OT_1$ wherein $T_1$ is as defined above; $Q_1$ is a $C_1$–$C_{18}$ alkyl radical; $R_{14}$ is a radical having the formula (1):

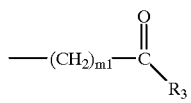
(1)

as defined above.

3. The sunscreen/cosmetic composition as defined by claim 2, said at least one compound of formula (I) being chosen from among:

(1) those in which the $A_1$ radical is a para-methoxyphenyl or para-ethoxyphenyl radical and the $R_1$ and $R_2$ radicals, which may be identical or different, are each a radical having the structure:

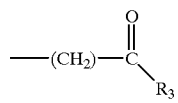

wherein $R_3$ is:

tert-butyloxy;

OH;

OM, wherein M is an alkali metal, or alkaline earth metal cation, or a cation selected from among copper, magnesium and zinc; p1 a group having the structure:

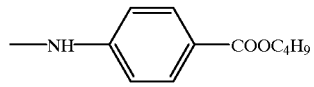

a group having the structure $O^-N^+(CH_2CH_2OH)_3$;
a group having the structure:

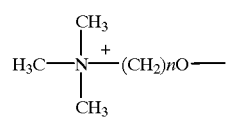

wherein n ranges from 2 to 16;

a group having the structure:

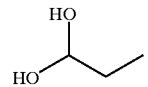

or a group having the structure:

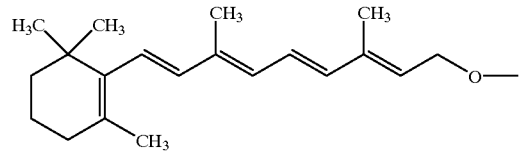

and (2) those in which the $A_1$ radical is a para-hydroxyphenyl radical and the $R_1$ and $R_2$ radicals simultaneously are each a group having the structure:

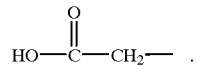

4. The sunscreen/cosmetic composition as defined by claim 2, said at least one bisresorcinyltriazine compound (I) comprising 2,4-bis{[4-(2-ethylhexyloxy)-2-hydroxy]phenyl}-6-(4-methoxyphenyl)-1,3,5-triazine; 2,4-bis{[4-(3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethyloxycarbonyl)phenylamino]-1,3,5-triazine; 2,4-bis{[4-(tris(trimethylsiloxy)silylpropyloxy)-2-hydroxy]phenyl}-6-(4-methoxyphenyl)-1,3,5-triazine; 2,4-bis{[4-(2"-methylpropenyloxy)-2-hydroxy]phenyl}-6-(4-methoxyphenyl)-1,3,5-triazine; 2,4-bis{[4-(1',1',1',3',5',5',5'-heptamethyltri-siloxy-2"-methylpropyloxy)-2-hydroxy]phenyl}-6-(4-methoxyphenyl)-1,3,5-triazine; 2,4-bis{[4-(3-(2-propyloxy)-2-hydroxypropyloxy)-2-hydroxy]phenyl}-6-[4-(ethoxycarbonyl)phenylamino]-1,3,5-triazine; 2,4-bis{[4-(2-ethylhexyloxy)-2-hydroxy]phenyl}-6-(1-methylpyrrol-2-yl)-1,3,5-triazine.

5. The sunscreen/cosmetic composition as defined by claim 4, said at least one bisresorcinyltriazine compound (I) comprising 2,4-bis{[4-(2-ethylhexyloxy)-2-hydroxy]phenyl}-6-(4-methoxyphenyl)-1,3,5-triazine; 2,4-bis{[4-(tris(trimethylsiloxy)silylpropyloxy)-2-hydroxy]phenyl}-6-(4-methoxyphenyl)-1,3,5-triazine; or 2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

6. The sunscreen/cosmetic composition as defined by claim 2, comprising from 0.1% to 15% by weight of said at least one bisresorcinyltriazine compound.

7. The sunscreen/cosmetic composition as defined by claim 6, comprising from 0.2% to 10% by weight of said at least one bisresorcinyltriazine compound.

8. The sunscreen/cosmetic composition as defined by claim 1, comprising at least one compound containing at least two benzoazolyl groups and having the following structural formula (II):

(II)

[structure shown with R², R³, R⁴, R⁵ on benzoazolyl ring, X', and R¹$_{p2}$—Z'$_{m5}$ substituent, bracketed with subscript n2]

in which Z' is an organic residue with a valency of $(p_2+n_2)$ comprising one or more double bonds which are positioned such that the double bond completes the system of double bonds of at least two benzoazolyl groups as defined inside the brackets, in order to form a completely conjugated unit; X' is S, O or NR⁶; R¹ is a hydrogen atom, a $C_1$–$C_{18}$ alkyl radical, a $C_1$–$C_4$ alkoxy radical a $C_5$–$C_{15}$ aryl radical, a $C_2$–$C_{18}$ acyloxy radical, SO₃Y' or COOY'; the R², R³, R⁴ and R⁵ radicals, which, may be identical or different, are each a nitro group or a radical R¹; R⁶ is a hydrogen atom, a $C_1$–$C_4$ alkyl radical, or a $C_1$–$C_4$ hydroxyalkyl radical; Y' is hydrogen atom, Li, Na, K, NH₄, ½Ca, ½Mg, ⅓Al, or a cation resulting from the neutralization of a free acid group by a nitrogenous organic base; $m_5$ is 0 or 1; $n_2$ is a number ranging from 2 to 6; $p_2$ is a number ranging from 1 to 4; with the proviso that $p_2+n_2$ does not exceed the value 6.

9. The sunscreen/cosmetic composition as defined by claim 8, wherein formula (II) the Z' radical is (a') an unsaturated linear aliphatic $C_2$–$C_6$ hydrocarbonaceous radical which can be interrupted by a $C_5$–$C_{12}$ aryl radical or a $C_4$–$C_{10}$ heteroaryl radical; (b') a $C_5$–$C_{15}$ aryl radical which can be interrupted by an unsaturated linear aliphatic $C_2$–$C_6$ hydrocarbonaceous radical; or (c;) a $C_3$–$C_{10}$ heteroaryl radical, with the proviso that the Z' radical may be substituted by $C_1$–$C_6$ alkyl, $C_1$–$C_6$ alkoxy, phenoxy, hydroxyl, methylenedioxy or amino radicals, the amino radicals optionally being substituted by one or two $C_1$–$C_5$ alkyl radicals.

10. The sunscreen/cosmetic composition as defined by claim 8, wherein formula (II) the Z' radical is selected from among: —CH=CH—

—CH=CH—CH=CH—

[structures: phenylene, biphenylene, naphthylene, coumarin-type, phenyl-CH=CH-phenyl, —CH=CH—phenylene—CH=CH—]

-continued

[structures: thiophene, furan, pyrrole (N-R⁶), trimethyltriazine]

11. The sunscreen/cosmetic composition as defined by claim 8, said at least one compound of formula (II) being selected from among the following compounds or salt thereof:

Compound 1

[bis-benzimidazole with one SO₃H group, HO₃S substituent]

Compound 2

[bis-benzimidazole with two SO₃H groups]

Compound 3

[bis-benzimidazole with SO₃H groups]

Compound 4

[bis-benzimidazole with four SO₃H groups]

Compound 5

[bis-benzoxazole with SO₃H group]

Compound 6

[bis-benzoxazole with two SO₃H groups]

Compound 7

[bis-benzoxazole with SO₃H groups]

Compound 8
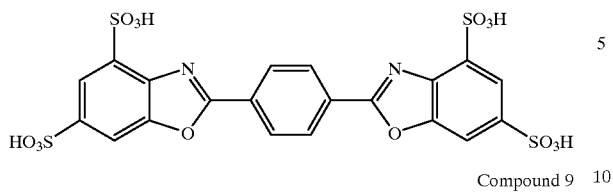
Compound 9
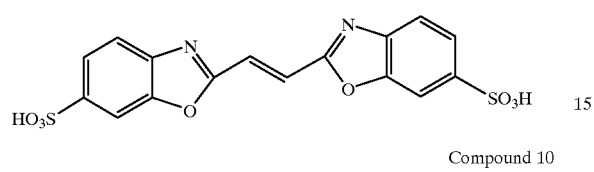
Compound 10
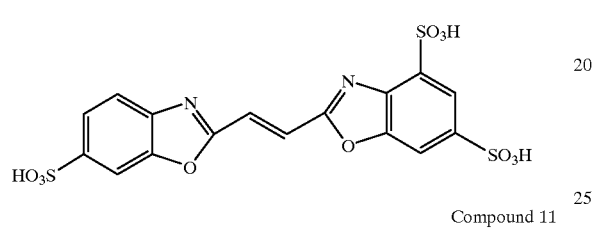
Compound 11
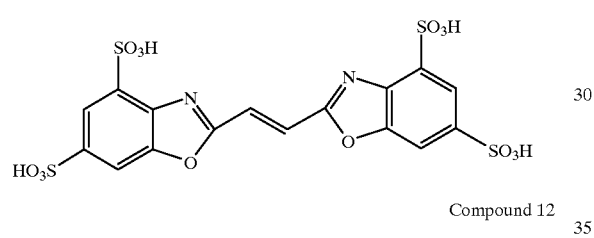
Compound 12
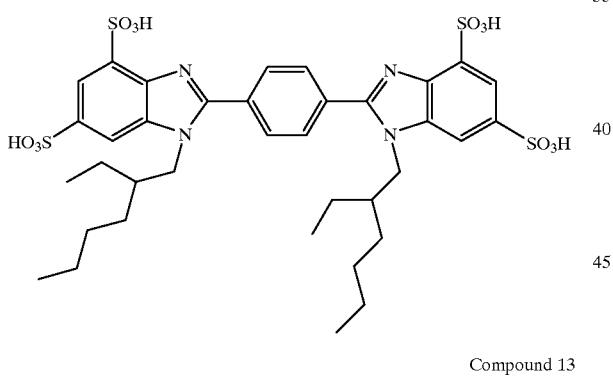
Compound 13
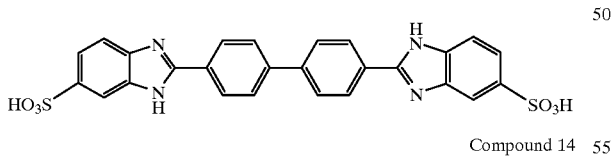
Compound 14
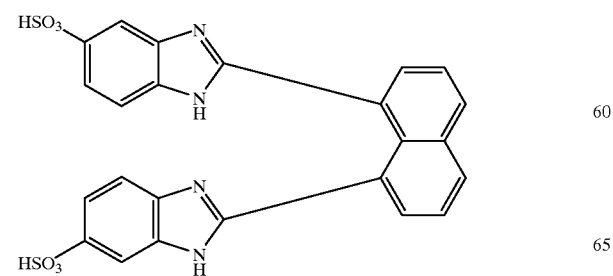
Compound 15
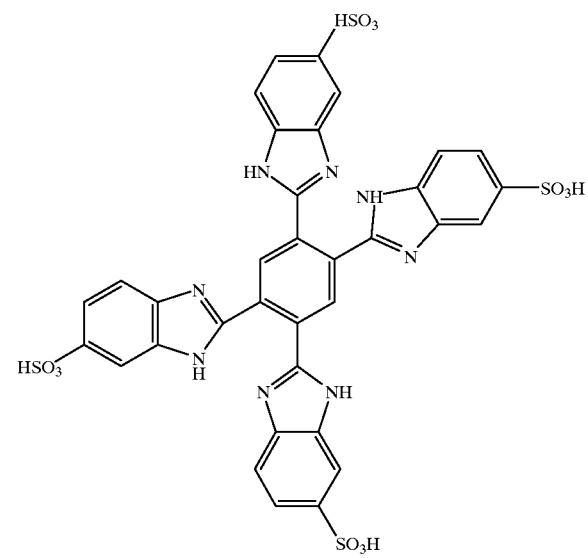
Compound 16
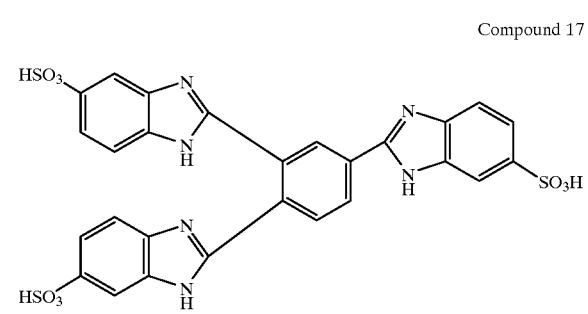
Compound 17
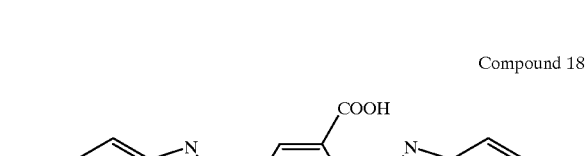
Compound 18
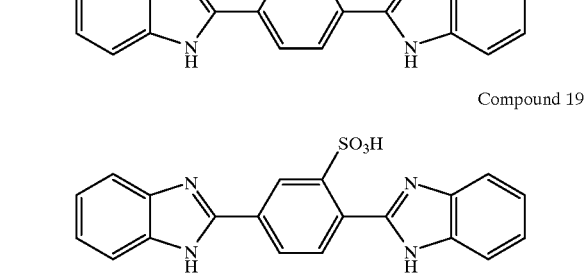
Compound 19

Compound 20

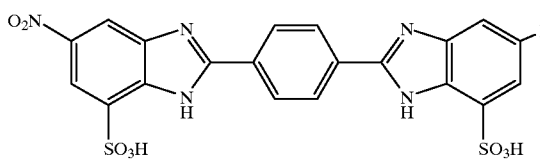

Compound 21

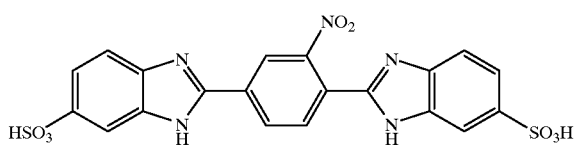

Compound 22

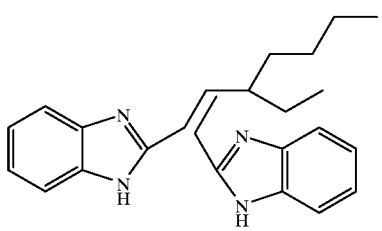

Compound 23

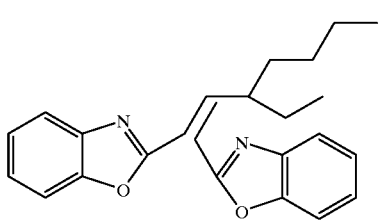

Compound 24

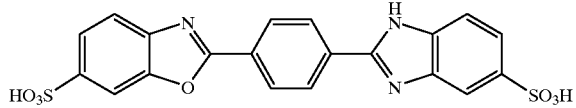

Compound 25

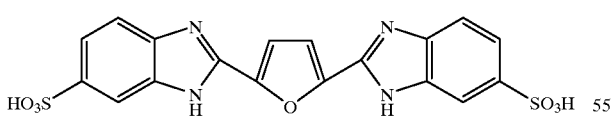

Compound 26

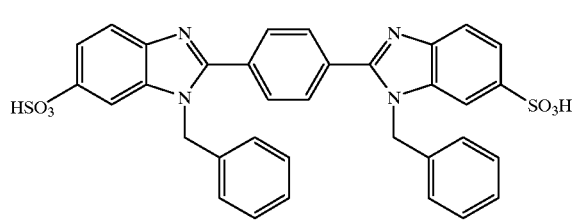

Compound 27

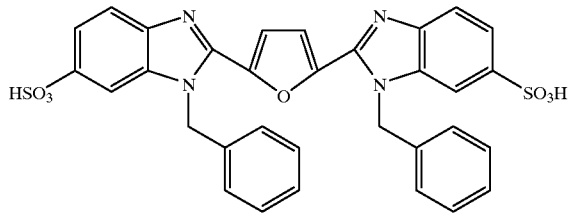

12. The sunscreen/cosmetic composition as defined by claim 8, said at least one compound of formula (II) comprising phenylene-1,4-bisbenzimidazole-3,3',5,5'-tetrasulfonic acid, or salt thereof, having the following structural formula:

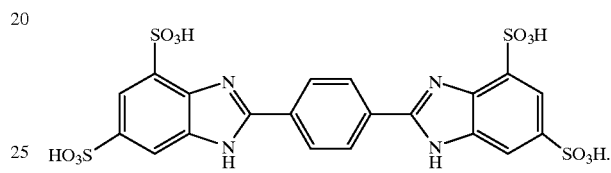

13. The sunscreen/cosmetic composition as defined by claim 1, comprising at least one compound containing at least two benzoazolyl groups and selected from among the following compounds or salt thereof:

Compound 28

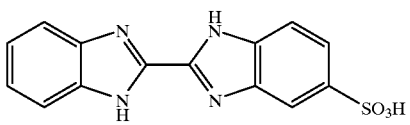

Compound 29

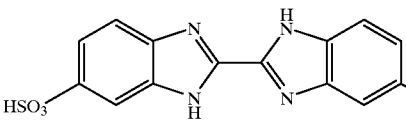

Compound 30

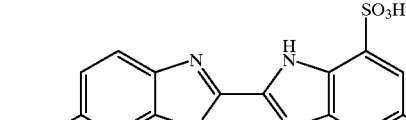

Compound 31

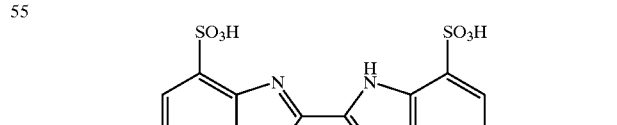

14. The sunscreen/cosmetic composition as defined by claim 1, comprising at least one compound containing at least one benzodiazolyl group and selected from among the following compounds or salt thereof:

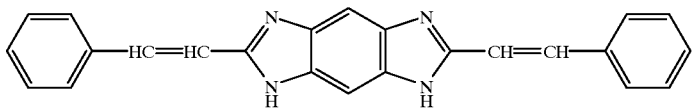

Compound 32

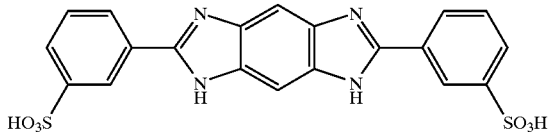

Compound 33

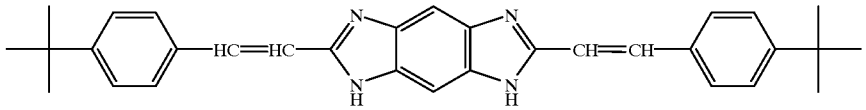

Compound 34

15. The sunscreen/cosmetic composition as defined by claim 1, comprising from 0.1% to 15% by weight of said at least one benzoazolyl/benzodiazolyl compound.

16. The sunscreen/cosmetic composition as defined by claim 15, comprising from 0.2% to 10% by weight of said at least one benzoazolyl/benzodiazolyl compound.

17. The sunscreen/cosmetic composition as defined by claim 1, formulated as an oil-in-water emulsion.

18. The sunscreen/cosmetic composition as defined by claim 1, formulated as a water-in-oil emulsion.

19. The sunscreen/cosmetic composition as defined by claim 1, further comprising at least one additional hydrophilic or lipophilic organic UV-A and/or UV-B sunscreen.

20. The sunscreen/cosmetic composition as defined by claim 19, further comprising at least one cinnamic derivative, salicylic derivative, camphor derivative, triazine derivative, benzophenone derivative, dibenzoylmethane derivative, benzimidazole derivative, β,β-diphenylacrylate derivative, p-aminobenzoic acid derivative, sunscreen polymer, or sunscreen silicone.

21. The sunscreen/cosmetic composition as defined by claim 1, further comprising a photoprotecting effective amount of particulates of at least one coated or uncoated inorganic pigment or nanopigment.

22. The sunscreen/cosmetic composition as defined by claim 21, said at least one pigment or nanopigment comprising titanium dioxide, zinc oxide, iron oxide, zirconium oxide, cerium oxide, or mixture thereof.

23. The sunscreen/cosmetic composition as defined by claim 1, further comprising at least one active agent for the artificial tanning and/or browning of human skin.

24. The sunscreen/cosmetic composition as defined by claim 1, further comprising at least one cosmetically acceptable adjuvant or additive.

25. The sunscreen/cosmetic composition as defined by claim 24, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative surfactant, filler, sequestering agent, polymer, propellant, basifying or acidifying agent, dye, colorant, or mixture thereof.

26. The sunscreen/cosmetic composition as defined by claim 1, comprising a nonionic vesicle dispersion, emulsion, cream, milk, gel, cream gel, ointment, suspension, dispersion, powder, solid stick or tube, foam or spray.

27. The sunscreen/cosmetic composition as defined by claim 1, comprising a makeup.

28. The sunscreen/cosmetic composition as defined by claim 27, comprising an anhydrous or aqueous solid or paste, emulsion, suspension, or dispersion.

29. The sunscreen/cosmetic composition as defined by claim 1, comprising a shampoo, lotion, gel, nonionic vesicle dispersion, hair lacquer, or rinse.

30. The sunscreen/cosmetic composition as defined by claim 1, having a sun protection factor of at least 2.

31. A regime/regimen for protecting human skin and/or hair against the deleterious effects of ultraviolet irradiation, comprising topically applying thereto an effective amount of the sunscreen/cosmetic composition as defined by claim 1.

32. A regime/regimen for protecting human skin and/or hair against the deleterious effects of solar radiation, comprising topically applying thereto an effective amount of the sunscreen/cosmetic composition as defined by claim 1.

* * * * *